United States Patent [19]

Youngs et al.

[11] Patent Number: 5,132,231
[45] Date of Patent: Jul. 21, 1992

[54] CARBON MONOXIDE DETECTOR USING A DERIVATIVE OF NI(TBC)

[75] Inventors: Wiley J. Youngs; Claire A. Tessier, both of Tallmadge; James D. Kinder, Cleveland Heights, all of Ohio

[73] Assignee: Case Western Reserve University, Cleveland, Ohio

[21] Appl. No.: 701,039

[22] Filed: May 16, 1991

[51] Int. Cl.$^5$ ...................... G01N 33/00; G01N 21/62
[52] U.S. Cl. ...................... 436/134; 436/171
[58] Field of Search .................. 436/134, 171, 84

[56] References Cited

U.S. PATENT DOCUMENTS

| | | | |
|---|---|---|---|
| 4,043,934 | 8/1977 | Shuler et al. | 252/186 |
| 4,251,225 | 2/1981 | Honda et al. | 436/134 |
| 4,256,694 | 3/1981 | McAllister et al. | 432/58 |
| 4,271,124 | 6/1981 | Specter | 432/68 |
| 4,617,277 | 10/1986 | Bohl | 436/34 |

FOREIGN PATENT DOCUMENTS 3052050  3/1988  Japan .................. 436/134

*Primary Examiner*—John W. Rollins

[57] ABSTRACT

A carbon monoxide detecting sensor of a derivative of Ni(TBC) which reacts with carbon monoxide to form a carbon monoxide adduct with a concomitant change in color.

11 Claims, No Drawings

CARBON MONOXIDE DETECTOR USING A DERIVATIVE OF Ni(TBC)

FIELD OF THE INVENTION

The invention relates to a carbon monoxide detecting sensor using a derivative of Ni(TBC), such as a para-dimethoxyphenyl substituted triene-triyne derivative, to react with carbon monoxide to form a carbon monoxide adduct with a concomitant color change in the derivative compound.

BACKGROUND OF THE INVENTION

Carbon monoxide remains a significant cause of human fatality because of its colorless and odorless characteristics. The human body has generally a low tolerance for carbon monoxide gas since a concentration of approximately 0.05% over an extended period of time or 1% for a few minutes could prove to be a fatal dosage for humans. Moreover, even a minor amount of carbon monoxide can be detrimental to human health. For example, when 50 parts per million of carbon monoxide are present in air, it may provide an environment that would be impossible to work in for more than 8 hours, while 200 parts per million of carbon monoxide present in the air could cause headaches within 3 or 4 hours. The combination of high toxicity along with the colorless and odorless characteristics of carbon monoxide makes it an extremely lethal gas since its presence in the atmosphere may not be detected by a human before it causes permanent damage.

Generally at the start of a fire, all the combustible substances contain carbon and in the initial stage of the fire, carbon monoxide is generally always present. In the initial stage of a fire, combustion is incomplete and carbon monoxide is generally present since there is usually insufficient heat for complete combustion. Thus the detection of carbon monoxide at the initial stage of a fire, could result in quick notification to a person in the area which could result in the saving of lives and the minimizing of property loss.

Carbon monoxide can be present in dangerous quantities in a wide variety of different environments such as homes, automobiles, aircraft, submarines, coal mines and the like. The serious threat posed by carbon monoxide, as evidenced by the appreciable annual fatalities due to exposure to an excessive amount of carbon monoxide, has resulted in the development of numerous quantitative procedures for detecting the presence and concentration of carbon monoxide in closed environments. A common type of analytical process would involve the oxidizing of the carbon monoxide to form carbon dioxide with the release heat providing a quantitative indication of the amount of carbon dioxide present. However, such devices required for this detection means are generally quite complex and expensive.

U.S. Pat. No. 2,487,077 discloses a carbon monoxide indicating composition, process and detection device. The composition consists essentially of a body of purified silica gel freed of substances oxidizable by hot concentrated nitric acid and having combined therein essentially dry residues of impregnation with a solution of palladium sulfate, sulfuric acid and ammonium molybdate, in proportions by weight of about 500 to 1600 parts gel, 5 to 50 parts acid containing about 1 part palladium, and about 10 to 60 parts molybdate. The composition is free of chloride ion.

Canadian Pat. No. 477,288 discloses a granular reagent adapted to undergo a color change in the presence of carbon monoxide consisting of a partly dehydrated granular product prepared by impregnating silica gel with a salt selected from the group consisting of alkali molybdates and tungstates, with a mineral acid, and with palladous halide.

U.S. Pat. No. 3,245,917 discloses a self-regenerating reagent for detecting the presence of carbon monoxide at a relative humidity of at least 20%, consisting essentially of a carrier of silica gel having adsorbed thereon palladium chloride and a regenerating amount of hydrochloric acid.

U.S. Pat. No. 4,043,934 discloses a self-regenerating reagent which, on contact with a reducing gas, oxidizes the gas and is reduced from an oxidized state to a reduced state. The reagent comprises a mixture of a palladium salt, a compound which includes a complex ion of a metal selected from the group consisting of molybdenum, tungsten and vanadium, and a salt of a metal selected from the group consisting of copper, nickel and iron, and a hydrophilic carrier for the mixture. Silica gel is among the possible carriers disclosed and carbon monoxide detection is one of the uses disclosed for the composition.

It is the object of the present invention to provide a novel material for detecting the presence of carbon monoxide.

It is another object of the present invention to provide a novel sensor having a high sensitivity to carbon monoxide.

It is another object of the present invention to provide a novel sensor that changes color upon the detection of carbon monoxide.

It is another object of the present invention to provide a carbon monoxide sensor material of a solid state derivative of Ni(TBC) which upon detecting the presence of carbon monoxide changes color.

It is another object of the present invention to provide a novel carbon monoxide sensor which retains its sensitivity over an appreciable period of time without substantial maintenance cost and which is cost effective to produce.

The above and further objects and advantages of this invention will become apparent upon consideration of the following description thereof.

SUMMARY OF THE INVENTION

The invention relates to a carbon monoxide sensor comprising a solid state derivative of Ni(TBC) having the following structure:

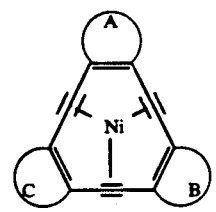

where each ring A, B and C is selected from the group consisting of a benzo ring, a heterocyclic ring, and a benzo ring with substituents and wherein said derivative of Ni(TBC) reacts with carbon monoxide to form a carbon monoxide adduct with a concomitant change in color in the derivative of Ni(TBC).

As used herein, substituents are alkoxides, alkyls of amines, thiols, silyl groups, nitro groups, halides and hydroxy. Examples of heterocycles are thiophene, quinones, furans, selenophenes, pyridines, pyrazins and pyrroles.

The novel sensor material of this invention functions such that a reaction occurs with carbon monoxide that produces a concomitant color change. Most solutions of Ni(TBC) will also react with oxygen thus making the removal of oxygen a necessary part of the sensor if it is to be used as a carbon monoxide sensor. The novel sensor material of this invention is a new derivative of Ni(TBC) that in the solid state reacts rapidly with carbon monoxide to form a carbon monoxide adduct with a concomitant change in color as for example from dark blue to brownish-yellow and that is stable to oxygen for several days.

Examples of phenyl derivatives of Ni(TBC) which are suitable for sensing carbon monoxide are represented by the general structure Ni(TBCR$^1_x$R$^2_y$) where R$^1$ and/or R$^2$ may equal dialkylamines, nitro groups, alkylthio groups, alkoxy groups, silyl groups, halides, and phosphines. Derivatives of interest of Ni(TBC) which contain heteroatoms in the aromatic rings are represented by Ni(cyclotriyne) where the rings A, B and C can be substituted and unsubstituted sulfur, oxygen, selenium and nitrogen heterocycles. An example of this last class is the thiophene derivative Ni(TTC) which was easily synthesized. Although this compound reacts faster with O$_2$ than with CO, this clearly shows that modifications of the external rings leads to considerable change in reactivity at the metal center.

Three derivatives of Ni(TBC) which have greater reversibility in their binding to carbon monoxide are:

(1) Ni(TBCR$^1_x$R$^2_y$) having the following structure in which R$^1$ and R$^2$ are selected from the group recited above.

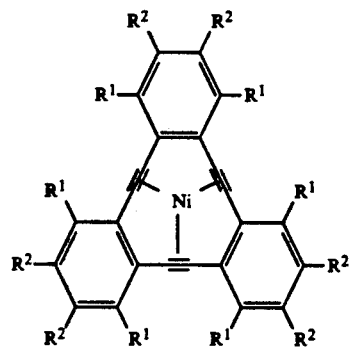

(2) Ni(cyclotriyne) having the following structure:

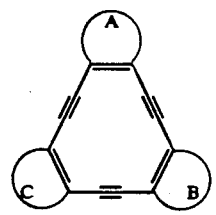

(3) Ni(TTC) or tri-thienyl derivative of Ni(TBC) having the following structure:

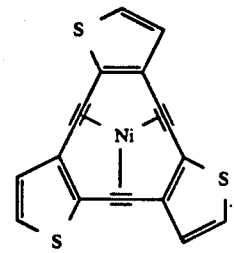

The compound that has given the best results for detecting carbon monoxide is para-dimethoxyphenyl substituted triene-triyne derivative having the following structure:

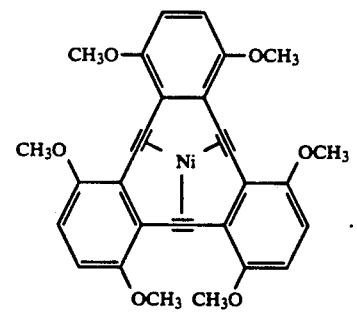

Another good compound for detecting carbon monoxide is a derivative of Ni(TBC) called Ni(TOC) which has the following structure:

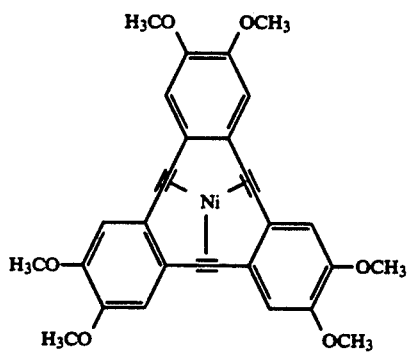

The A, B and C rings are intended to represent a variety of ring sizes (5 or 6 membered rings), with each ring being, for example, an all carbon or heterocyclic ring or a ring with electron withdrawing and/or electron donating substituents. Rings A, B and C could all be the same as in the para-dimethoxyphenyl substituted triene-triyne derivative, or two rings could be the same as in the following structure:

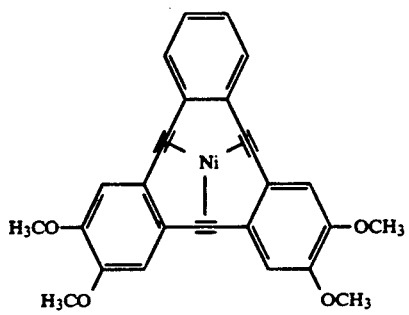

or all three rings could be different as in the following structure.

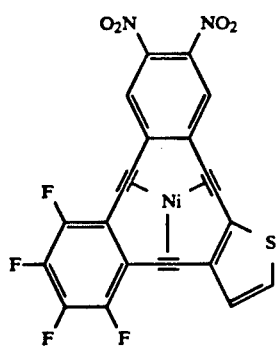

A primary requirement of the sensor material is that it is in the solid state and have good sensitivity to react rapidly with carbon monoxide to form a carbon monoxide adduct with a concomitant color change. For most applications the sensor material could detect concentrations of carbon monoxide as low as 100 parts per million (ppm) in a gaseous medium. Preferably the sensor material could detect concentrations of carbon monoxide as low as 50 ppm in a gaseous medium and most preferably a concentration of carbon monoxide as low as 10 ppm in a gaseous medium. Upon the detection of the carbon monoxide, the sensor will change color thereby providing a visual indication that carbon monoxide is present. The sensor material could be coupled to conventional electronic circuitry which can provide an audio signal once the color of the sensor material changes and/or provide a visual light signal once the color of the sensor material changes. The sensor material can be used in any application to detect the presence of carbon monoxide, even at extremely small concentrations, in a gaseous medium.

Using the sensor materials of this invention carbon monoxide can be detected in air without the necessity of removing oxygen by chemical or other means. Another benefit of some of the carbon monoxide detecting materials of this invention is that derivatives of Ni(TBC) may bond carbon monoxide reversibly thereby permitting the material to be reusable as a carbon monoxide sensor.

EXAMPLE 1

A derivative of Ni(TBC), Ni(TPC) was synthesized by combining the TPC ligand with nickel bis(cyclooctadiene). The TPC ligand was synthesized by the Stephens-Castro coupling of 2-iodo-3,6-dimethoxyphenylacetylene.

The compound formed was solid and had a dark blue color. The Ni(TPC) was exposed to air containing about 100 ppm carbon monoxide and the carbon monoxide formed a carbon monoxide adduct with a concomitant color change to brownish-yellow. The Ni(TPC) was exposed to air for several days and did not effectively react with the oxygen in the air.

EXAMPLE 2

A derivative of Ni(TBC), Ni(TOC) was synthesized by combining the TOC ligand with nickel bis (cyclooctadiene). The TOC ligand was synthesized by the Stephens-Castro coupling of 2-iodo-4,5-dimethoxyphenylacetylene.

The compound formed was solid and had a dark blue color. The para-dimethoxyphenyl substituted triene-triyne derivative was exposed to air containing about 100 ppm carbon monoxide and the carbon monoxide formed a carbon monoxide adduct with a concomitant color change to brownish-yellow. The Ni(TPC) was exposed to air for several days and did not effectively react with the oxygen in the air.

EXAMPLE 3

A derivative of Ni(TBC), NI(TTC) was synthesized by combining the TTC ligand with nickel bis(cyclooctadiene). The TTC ligand was synthesized by the Stephens-Castro coupling of 2-iodo-3,6-dimethoxyphenylacetylene. Ni(TTC) reacts more rapidly with oxygen then with carbon monoxide.

As many possible embodiments may be made by this invention without departing from the scope thereof, it being understood that all matter set forth is to be interpreted as illustrative and not in a limiting sense. For example, the material of this invention could be used in devices for the home, assembled in a badge sized detector for use in plants and mines or any other application.

What is claimed:

1. A carbon monoxide sensor comprising a solid state derivative of Ni(TBC) having the following structure:

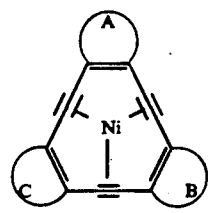

where each ring A, B and C is selected from the group consisting of a benzo ring, a heterocyclic ring, and a benzo ring with at least one substituent and wherein said derivative of Ni(TBC) reacts with carbon monoxide to form a carbon monoxide adduct with a concomitant change in color in the derivative of Ni(TBC).

2. The carbon monoxide sensor of claim 1 wherein the substituent is selected from the group consisting of alkoxides, alkyls of amines, thiols, silyl groups, nitro groups, halides and hydroxy.

3. The carbon monoxide sensor of claim 1 comprising a phenyl derivative of Ni(TBC) having the general structure Ni(TBCR$^1_x$R$^2_y$) where $R^1$ and $R^2$ are each selected from the group consisting of dialkylamine, nitro group, alkylthio group, alkoxy group, silyl group, halide, and phosphine.

4. The carbon monoxide sensor of claim 1 wherein the solid state derivative of Ni(TBC) is Ni(cyclotriyne).

5. The carbon monoxide sensor of claim 1 wherein the solid state derivative of Ni(TBC) is tri-thienyl derivative of Ni(TBC) having the following structure:

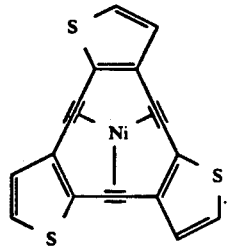

6. The carbon monoxide sensor of claim 1 wherein the solid state derivative of Ni(TBC) is para-dimethoxyphenyl substituted triene-triyne derivative having the following structure:

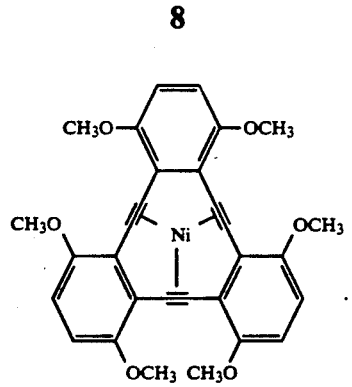

7. The carbon monoxide sensor of claim 1 wherein the solid state derivative of Ni(TBC) is Ni(TOC) having the following structure:

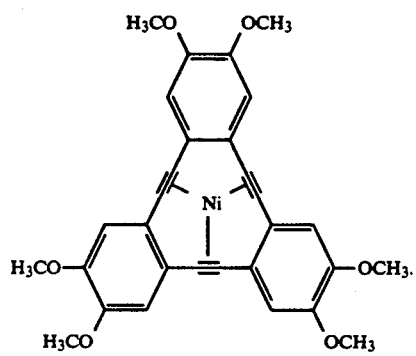

8. The carbon monoxide sensor of claim 1 wherein the A, B and C rings are all the same.

9. The carbon monoxide sensor of claim 1 wherein two of the A, B and C rings are the same.

10. The carbon monoxide sensor of claim 1 wherein the A, B and C rings are all different.

11. The carbon monoxide sensor of claim 1 wherein the derivative of Ni(TBC) changes color upon the detection of carbon monoxide of about 100 parts per million in a gaseous medium.

* * * * *